United States Patent [19]
Bivens et al.

[11] Patent Number: 5,662,825
[45] Date of Patent: Sep. 2, 1997

[54] USE OF 1,1,1,3,3,3-HEXAFLUOROPROPANE IN CENTRIFUGAL COMPRESSORS

[75] Inventors: Donald Bernard Bivens, Kennett Square, Pa.; Richard Edward Fernandez, Bear, Del.; Mark Brandon Shiflett, Newark, Del.; Tuneen Chisolm-Carter, New Castle, Del.

[73] Assignee: E. I. Du Pont de Nemours and Company, Wilmington, Del.

[21] Appl. No.: 379,108

[22] Filed: Jan. 27, 1995

Related U.S. Application Data

[63] Continuation of Ser. No. 165,562, Dec. 10, 1993, abandoned, which is a continuation of Ser. No. 788,464, Nov. 6, 1991, abandoned.

[51] Int. Cl.$^6$ .................................................. C09K 5/04
[52] U.S. Cl. ...................................... 252/67; 62/114
[58] Field of Search .............................. 252/67; 62/114

[56] References Cited

U.S. PATENT DOCUMENTS

| | | | |
|---|---|---|---|
| 4,312,188 | 1/1982 | Swenson et al. | 62/160 |
| 4,541,943 | 9/1985 | Powell | 252/67 |
| 4,668,830 | 5/1987 | Desbois | 568/655 |
| 4,687,588 | 8/1987 | McLinden et al. | 252/67 |
| 5,076,064 | 12/1991 | Kopko | 62/77 |

FOREIGN PATENT DOCUMENTS

| | | |
|---|---|---|
| 2009169 | 8/1990 | Canada . |
| 445611 | 9/1991 | European Pat. Off. . |
| 272086 | 11/1990 | Japan . |
| 2-272086 | 11/1990 | Japan . |
| 93/09200 | 5/1993 | WIPO . |

OTHER PUBLICATIONS

Kopko, "Beyond CFCs: Extending the Search for New Refrigerants", Proceedings of ASHRAE's 1989 CFC Technology Conference, Gaithersburg, MD, 39–46, Sep. 1989.

Schultz, "The Polytropic Analysis of Centrifugal Compressors", Journal of Engineering for Power, Transactions of the ASME, Series A, 84, 69–82, Jan. 1962.

McLinden et al., "Quest for Alternatives", ASHRAE Journal, 32–42, Dec. 1987.

Fischer et al., "Energy and Global Warming Impacts CFC Alternative Technologies", Sponsored by the Alternative Fluorocarbons Environmental Acceptability Study and the U.S. Development of Energy, 3.1–3–13, Dec. 1991.

Fischer et al., "Energy–Use Impact of Chlorofluorocarbon Alternatives", U.S. Department of Commerce, National Technical Information Service, Feb. 1989.

Transactions, American Society of Heating, Refrigerating and Air–Conditioning Engineers, vol. 65, 355–377, 1959 no month available.

HVAC Systems and Equpment, ASHRAE Handbook, 34.25–34.35, 1996.

Derwant's abstract No. 90–373, 625/50, week 9050, Abstract of JP 2272086 (Asahi Glass KK), 6 Nov. 1990, and JP A 2272086.

Chem. Abs. 83(2):27097n, "Mass Spectral Correlations of Halogenated 1,1,1,3,3,3–hexafluoropropanes and 1,1,1–trifluoroethanes". Naae et al., 1974 no month available.

Chem. Abs. 120:273889, "Modeled performance of non-chlorinated substitutes for CFC11 and CFC12 in centrifugal chillers", Int. J. Refrig. 17(1), 40–8 no month available 1994.

*Primary Examiner*—Christine Skane

[57] ABSTRACT

1,1,1,3,3,3-Hexafluoropropane is disclosed as a refrigerant.

2 Claims, No Drawings

USE OF 1,1,1,3,3,3-HEXAFLUOROPROPANE IN CENTRIFUGAL COMPRESSORS

This is a continuation of application Ser. No. 08/165,562 filed Dec. 10, 1993, now abandoned, which is a continuation of application Ser. No. 07/788,464 filed Nov. 6, 1991, abandoned.

FIELD OF THE INVENTION

This invention relates to the use of 1,1,1,3,3,3-hexafluoropropane (HFC-236fa) as a refrigerant, heat transfer media, gaseous dielectric sterilant carrier, polymerization media, particulate removal fluid, carrier fluid, buffing abrasive agent, displacement drying agent, and as a power cycle working fluid. More particularly, it relates to 1,1,1,3,3,3-hexafluoropropane as a highly effective and potentially environmentally safe refrigerant for use in refrigeration equipment utilizing centrifugal compression.

BACKGROUND OF THE INVENTION

Mechanical refrigeration is primarily an application of thermodynamics wherein a cooling medium, such as a refrigerant, goes through a cycle so that it can be recovered for reuse. Commonly used cycles include vapor-compression, absorption, stem-jet or stem-ejector, and air.

There are various types of compressors that may be used in refrigeration applications. Compressors can be generally classified as reciprocating, rotary, jet, centrifugal, or axial-flow, depending on the mechanical means to compress the fluid, or as positive-displacement or dynamic, depending on how the mechanical elements act on the fluid to be compressed.

A centrifugal compressor uses rotating elements to accelerate the refrigerant radially, and typically includes an impeller and diffuser housed in a casing. Centrifugal compressors usually take fluid in at an impeller eye, or central inlet of a circulating impeller, and accelerate it radially outwardly. Some static pressure rise occurs in the impeller, but most of the pressure rise occurs in the diffuser section of the casing, where velocity is converted to static pressure. Each impeller-diffuser set is a stage of the compressor. Centrifugal compressors are built with from 1 to 12 or more stages, depending on the final pressure desired and the volume of refrigerant to be handled.

The pressure ratio, or compression ratio, of a compressor is the ratio of absolute discharge pressure to the absolute inlet pressure. Pressure delivered by a centrifugal compressor is practically constant over a relatively wide range of capacities.

Unlike a positive displacement compressor, a centrifugal compressor depends entirely on the centrifugal force of the high speed impeller to compress the vapor passing through the impeller. There is no positive displacement, but rather what is called dynamic-compression.

The pressure a centrifugal compressor can develop depends on the tip speed of the impeller. Tip speed is the speed of the impeller measured at its tip and is related to the diameter of the impeller and its revolutions per minute. The capacity of the centrifugal compressor is determined by the size of the passages through the impeller. This makes the size of the compressor more dependent on the pressure required than the capacity.

Because of its high speed operation, a centrifugal compressor is fundamentally a high volume, low pressure machine. A centrifugal compressor works best with a low pressure refrigerant, such as trichlorofluoromethane (CFC-11). When CFC-11 is used as the refrigerant, suction pressure in the compressor is from about 18 to 25 inches of vacuum depending on the evaporator temperature required, and the discharge pressure is near atmospheric pressure. A single stage impeller can be used with CFC-11 for air conditioning suction temperatures.

A two-stage impeller is common for many conditions. In operation, the discharge of the first stage impeller goes to the suction intake of a second impeller. Each stage can build up a compression ratio of about 4 to 1, that is, the absolute discharge pressure can be 4 times the absolute suction pressure.

Centrifugal compressors range in size from 200 to 10,000 kilowatts of refrigeration capacity. For applications requiring more or less refrigeration capacity than CFC-11, 1,2,2-trichloro-trifluoroethane (CFC-113) or 1,2-dichlorotetrafluoroethane (CFC-114) can be used as the refrigerant in place of CFC-11 without changing the compressor except for providing a properly-sized motor.

A proposed world-wide reduction in the production of fully halogenated chlorofluorocarbons such as CFC-11, CFC-113, and CFC-114, has developed an urgent need for alternative, more environmentally acceptable products.

Large investments have been made in centrifugal compressors that were designed for CFC-11, CFC-113, or CFC-114. A centrifugal compressor is designed for the refrigerant with which it is to be used. That is, a centrifugal compressor is typically designed by first selecting a refrigerant, and then determining the desired refrigeration capacity and power source. Once these variables are known, the diameter of the impeller, the size of the impeller opening, and the number of stages are designed to achieve the desired refrigeration capacity.

A problem with replacing chloroflurocarbons with alternative refrigerants for use in existing centrifugal compressors that unless the alternative refrigerant matches certain physical criteria, the alternative refrigerant will not work in the existing centrifugal compressor. Important criteria include the "tip speed" of a refrigerant, meaning the speed of the impeller as measured at its tip for a given centrifugal compressor, and the density and molecular weight of the refrigerant.

If it is desired to replace a refrigerant in a centrifugal compressor, and the replacement refrigerant does not perform as well the original refrigerant, it is possible to design a compressor for the replacement refrigerant and to replace the original compressor. However, replacing an existing compressor is not possible in all cases. For example, a centrifugal compressor may be so large (such as is used in the cooling system of large buildings) that it cannot be replaced by a redesigned compressor. In such cases, the replacement refrigerant must work in the original compressor.

DETAILED DESCRIPTION

The present invention relates to the discovery that 1,1,1,3,3,3-hexafluoropropane (HFC-236fa) may be used as a refrigerant, and more particularly as a refrigerant for use in centrifugal compression refrigeration equipment.

There are three important choices in selecting or designing a centrifugal compressor: the diameter of the impeller, which means the length from the end of one of the impeller blades to the end of an opposite blade, the width of the passage in the impeller, and the refrigerant. The impeller and refrigerant must be selected in a combination that best suits a desired application.

The diameter of the impeller depends on the discharge pressure that must be achieved. For a given rotative speed, a large impeller diameter provides a higher tip speed, which results in a higher pressure ratio. Tip speed means the tangential velocity of the refrigerant leaving the impeller. If a centrifugal compressor that uses CFC-114 as a refrigerant is driven by an electric motor operating at 85 revolutions per second (r/s), and the impeller diameter of the compressor is 0.575 meters, the impeller generates a tip speed of 153.4 m/s.

It is desirable to find a "drop-in" replacement for CFC-114, that is, a refrigerant that may be used in equipment designed for CFC-114 and that performs similarly to CFC-114. To perform as well as CFC-114 in existing equipment, a refrigerant must be such that when it is used, the impeller achieves a tip speed that matches, or nearly matches, the tip speed of the impeller when CFC-114 is used. HFC-236fa provides a tip speed identical or nearly identical to the tip speed of CFC-114 when the two refrigerants are used in the same operating equipment.

Another important factor in the design of a centrifugal compressor is the width of passage in the impeller. Increasing the size of this passage increases the capacity of the compressor, but also increases the power required by the compressor. Centrifugal compressors are designed to maintain high efficiencies, especially when the compressors are used with machines that operate at low capacities. One way to increase the efficiency of the compressor without increasing the width between the impeller blades is to use a refrigerant with a low density, such as CFC-114, which reduces the friction on the narrow impeller faces relative to the flowrate through the impeller.

The liquid density of CFC-114 is 1.555 g/cc at room temperature, and the liquid density of 1,1,1,3,3,3-hexafluoropropane is 1.230 g/cc at room temperature. The lower density of HFC-236fa may increase the efficiency of a centrifugal compressor at low capacities, and at least should allow the centrifugal compressor to operate at the same efficiency as when CFC-114 is used.

Also, the molecular weight of the refrigerant is an important design consideration for centrifugal compressors. The molecular weight of CFC-114 is 170.9 and the molecular weight of 1,1,1,3,3,3-hexafluoropropane is 152.0.

Another important physical property of HFC-236fa is that it boils at −15° C., which is close to the boiling point of 3.6° C. of CFC-114.

EXAMPLE 1

Tip Speed to Develop Pressure

Tip speed can be estimated by making some fundamental relationships for refrigeration equipment that uses centrifugal compressors. The torque a impeller ideally imparts to a gas is defined as $$T = m^*(v_2^* r_2 - v_1^* r_1)$$ Equation 1 where

T=torque, N*m m=mass rate of flow, kg/s $v_2$=tangential velocity of refrigerant leaving impeller, m/s $r_2$=radius of exit impeller, m $v_1$=tangential velocity of refrigerant entering impeller, m/s $r_1$=radius of inlet of impeller, m Assuming the refrigerant enters the impeller in an essentially radial direction, the tangential component of the velocity $v1=0$, therefore $$T = m^* v_2 {\cdot} r_2$$ Equation 2

The power required at the shaft is the product of the torque and the rotative speed $$P = T^* w$$ Equation 3 where

P=power, W w=rotative speed, r/s therefore, $$P = T^* w = m^* v_2^* r_2^* w$$ Equation 4

At low refrigerant flow rates, the tip speed of the impeller and the tangential velocity of the refrigerant are nearly identical; therefore $$r_2^* w = v_2$$ Equation 5 and $$P = m^* v_2^* v_2$$ Equation 6

Another expression for ideal power is the product of the mass rate of flow and the isotropic work of compression, $$P = m^* H_i^* (1000 J/kJ)$$ Equation 7 where $H_i$=Difference in enthalpy of the refrigerant from a saturated vapor at the evaporating condition to saturated condensing conditions, kJ/kg.

Combining the two expressions Equation 6 and 7 produces, $$v_2^* v_2 = 1000^* H_i$$ Equation 8

Although equation 8 is based on some fundamental assumptions, it provides a good estimate of the tip speed of the impeller and provides an important way to compare tip speeds of refrigerants.

Table 1 shows theoretical speeds for dichlorotetrafluoroethane (CFC-114), 1,1,1,3,3,3-hexafluoropropane (HFC-236fa), and ammonia. The conditions assumed for this comparison are that the refrigerant is compressed from a saturated vapor at 4.4 degrees Celsius (40 degrees Fahrenheit) to a pressure corresponding to a condensing temperature of 43.3 degrees Celsius (110 degrees Fahrenheit). These are typical conditions under which a centrifugal chiller performs.

Also, the diameter of the impeller is 0.575 meters, and, for CFC-114, the compressor is driven by an electric motor operating at 85 r/s. For HFC-236fa, the compressor is driven by a motor operating at 88 r/s.

TABLE 1

|  | CFC-114 | HFC-236fa | Ammonia |
| --- | --- | --- | --- |
| Hi, kJ/kg | 3.5 | 25.4 | 43.5 |
| v2, m/s | 153.4 | 159.3 | 208.5 |

To provide refrigeration performance similar to CFC-114 using existing equipment designed for CFC-114, a refrigerant must provide a tip speed that matches or nearly matches the tip speed generated using CFC-114. Using HFC-236fa as a drop in replacement in equipment designed for CFC-114 and having a wheel diameter of 0.575 meters, HFC-236fa produces a tip speed of 159.3 m/s with a motor operating speed of 88 r/s. This operating speed could be accommodated using the same motor as used in the present equipment. Alternatively, the wheel size can be increased to 0.6 meters to operate the motor at 85 r/s. Thus, it is possible to use HFC-236fa in existing equipment designed for CFC-114 with little or no equipment modification.

EXAMPLE 2

This example compares the performance of HFC-236fa to CFC-114 in a centrifugal chiller. The size of the impeller in this example is 0.762 meters.

|  | CFC-114 | HFC-236fa |
|---|---|---|
| evaporator temperature, °C. | 4.4 | 4.4 |
| evaporator pressure, kPa | 106.5 | 125.8 |
| net refrigeration effect, kJ/kg | 118 | 130 |
| refrigerant flow, kg/s | 35.3 | 31.9 |
| compressor flow rate (inlet) l/s | 4282 | 3648 |
| polytropic head pressure (m of head of the gas) | 1846 | 2056 |
| relative tip speed, m/s | 147.1 | 155.2 |
| acoustic velocity, m/s | 111.6 | 124.1 |
| condenser temperature, °C. | 43.3 | 43.3 |
| condenser pressure, kPa | 374.3 | 442.8 |
| kilowatts | 942 | 957 |
| kilowatts/kilowatts of refrigeration | 0.227 | 0.231 |

These data show that HFC-236fa may be used as a replacement for CFC-114. Some modifications to the motor for compressors designed for use with CFC-114 may be necessary to use HFC-236fa as a drop in replacement, such as gearing up or gearing down the motor.

In summary, this invention relates to the discovery that HFC-236fa may be used as a refrigerant. A particularly useful application of the refrigerant is in refrigeration equipment, such as chillers, that use centrifugal compressors designed for use with CFC-11, CFC-113, and CFC-114, with replacement of CFC-114 being preferred.

We claim:

1. A process for producing refrigeration comprising providing a centrifugal compressor designed to use 1,2-dichloro-tetrafluoroethane as a refrigerant compressing a replacement refrigerant in the centrifugal compressor, and evaporating the refrigerant in the vicinity of a body to be cooled, wherein said replacement refrigerant consists essentially of 1,1,1,3,3,3-hexafluoropropane.

2. A process for producing refrigeration comprising providing a centrifugal compressor designed to use 1,2,2-trichlorotrifluoroethane as a refrigerant, compressing a replacement refrigerant in the centrifugal compressor, and evaporating the refrigerant in the vicinity of a body to be cooled:

wherein said replacement refrigerant consists essentially of 1,1,1,3,3,3-hexafluoropropane.

\* \* \* \* \*